United States Patent
Novorita et al.

(10) Patent No.: US 12,431,742 B2
(45) Date of Patent: Sep. 30, 2025

(54) SURGICAL INSTRUMENT WIRELESS CHARGING SYSTEM

(71) Applicant: Stryker Corporation, Kalamazoo, MI (US)

(72) Inventors: James Novorita, Otsego, MI (US); Thomas Puvogel, Kalamazoo, MI (US); Burton Judson, Kalamazoo, MI (US); Ian Dalrymple, Comstock Township, MI (US)

(73) Assignee: Stryker Corporation, Portage, MI (US)

( * ) Notice: Subject to any disclaimer, the term of this patent is extended or adjusted under 35 U.S.C. 154(b) by 653 days.

(21) Appl. No.: 17/885,602

(22) Filed: Aug. 11, 2022

(65) Prior Publication Data

US 2024/0055905 A1 Feb. 15, 2024

(51) Int. Cl.
*H01M 10/44* (2006.01)
*H01M 10/46* (2006.01)
(Continued)

(52) U.S. Cl.
CPC .......... *H02J 50/402* (2020.01); *H02J 7/0013* (2013.01); *H02J 7/0044* (2013.01); *H02J 50/10* (2016.02);
(Continued)

(58) Field of Classification Search
CPC ...... H02J 7/0013; H02J 7/0044; H02J 7/0042; H02J 50/402; H02J 50/10; H02J 50/80;
(Continued)

(56) References Cited

U.S. PATENT DOCUMENTS

| | | | | |
|---|---|---|---|---|
| 6,018,227 A | * | 1/2000 | Kumar | H02J 7/00036 320/112 |
| 6,847,190 B2 | * | 1/2005 | Schaefer | H02J 7/0042 320/107 |

(Continued)

FOREIGN PATENT DOCUMENTS

| | | | | |
|---|---|---|---|---|
| EP | 3242376 A1 | * | 11/2017 | A61L 2/26 |
| JP | 2022527478 A | * | 6/2022 | |

(Continued)

OTHER PUBLICATIONS

Altamirano, Daniel et al., "Evaluation of the Effects of Co-Channel Interference on the Bit Error Rate of Cellular Networks", https://www.inatel.br/revista/busca/257-r-t-vol-13-n-02-6-evaluation-of-the-effects-s972866-1/file, vol. 13, No. 2, Dec. 2011, 5 pages.

(Continued)

*Primary Examiner* — Edward Tso
(74) *Attorney, Agent, or Firm* — Howard & Howard Attorneys PLLC

(57) ABSTRACT

Wireless charging systems and methods for wirelessly charging batteries for powering surgical instruments. A wireless charging device includes a housing defining wireless charging bays for receiving and charging multiple surgical instrument batteries simultaneously. Power transfer coils and RF antennas are disposed in the housing, with each of the wireless charging bays being associated with a different power transfer coil for wirelessly charging a received battery and with a different RF antenna for wirelessly communicating with the received battery. The RF antennas are each configured to communicate in a same frequency band. The wireless charging device is configured to communicate with a battery received by a first of the wireless charging bays using the RF antenna associated with the first wireless charging bay during a first period while preventing the RF antenna associated with a second of the wireless (Continued)

charging bays from communicating with a battery received by the second wireless charging bay. Responsive to the first period elapsing, the wireless charging device is configured to communicate with the battery received by the second wireless charging bay using the RF antenna associated with the second wireless charging bay during a second period while preventing the RF antenna associated with the first wireless charging bay from communicating with the battery received by the first wireless charging bay.

20 Claims, 8 Drawing Sheets

(51) Int. Cl.
  *H02J 7/00* (2006.01)
  *H02J 50/10* (2016.01)
  *H02J 50/40* (2016.01)
  *H02J 50/80* (2016.01)
  *A61B 17/00* (2006.01)

(52) U.S. Cl.
  CPC ..... *H02J 50/80* (2016.02); *A61B 2017/00734* (2013.01)

(58) Field of Classification Search
  CPC ....... H02J 50/90; H02J 2310/23; A61B 50/20; A61B 90/98; A61B 2017/00734
  USPC ........................ 320/107, 108, 114, 115, 116
  See application file for complete search history.

(56) References Cited

U.S. PATENT DOCUMENTS

| | | | |
|---|---|---|---|
| 8,928,462 | B2 | 1/2015 | Gravelle et al. |
| 10,235,616 | B2 | 3/2019 | Cruickshanks et al. |
| 10,236,709 | B2* | 3/2019 | Decker ................. H02J 50/00 |
| 11,316,371 | B1 | 4/2022 | Partovi et al. |
| 2009/0003294 | A1 | 1/2009 | Zhu et al. |
| 2009/0245221 | A1 | 10/2009 | Piipponen |
| 2011/0057609 | A1* | 3/2011 | Smith .................. H02J 7/0045 |
| | | | 320/108 |
| 2011/0304434 | A1 | 12/2011 | Kohli et al. |
| 2014/0148095 | A1 | 5/2014 | Smith et al. |
| 2021/0257856 | A1* | 8/2021 | Ng ........................ H02J 7/0047 |

FOREIGN PATENT DOCUMENTS

| | | | | |
|---|---|---|---|---|
| KR | 20210146972 A | * | 12/2021 | |
| WO | WO-2019067539 A1 | * | 4/2019 | ............. H02J 50/10 |
| WO | 2019088327 A1 | | 5/2019 | |
| WO | 2020198666 A2 | | 10/2020 | |

OTHER PUBLICATIONS

English language abstract and machine-assisted English translation for WO 2019/088327 A1 extracted from espacenet.com database on Aug. 11, 2022, 5 pages.

Rohde & Schwarz, "Near Field Communication (NFC) Technology and Measurements White Paper", https://cdn.rohde-schwarz.com/pws/dl_downloads/dl_application/application_notes/1ma182/1MA182_5E_NFC_WHITE_PAPER.pdf, Jun. 2011, 18 pages.

* cited by examiner

140

SURGICAL INSTRUMENT WIRELESS CHARGING SYSTEM

BACKGROUND

A surgical procedure often involves the use of multiple surgical instruments, many of which are battery-powered to provide increased maneuverability during the procedure. It is thus desirable for a system capable of receiving and charging multiple surgical instrument batteries at substantially the same time, and that does so in a particularly reliable and convenient manner in the context of a surgical procedure.

SUMMARY

In one aspect, a wireless charging system is provided. The wireless charging system includes a plurality of wirelessly chargeable batteries for powering surgical instruments; a medical package holding the batteries in a sterilized state; and a wireless charging device configured to receive the medical package holding the batteries in the sterilized state for charging the batteries without the batteries exiting the sterilized state. The wireless charging device comprises: a housing defining a plurality of wireless charging bays for charging the batteries, the wireless charging bays arranged so that each of the batteries aligns with a different one of the wireless charging bays when the medical package holding the batteries in the sterilized state is received by the wireless charging device; a plurality of power transfer coils disposed in the housing, each of the wireless charging bays being associated with a different one of the power transfer coils for wirelessly charging the battery aligned with the wireless charging bay; and a plurality of RF antennas disposed in the housing, each of the wireless charging bays being associated with a different one of the RF antennas for wirelessly communicating with the battery aligned with the wireless charging bay according to a proximity-based wireless communications protocol, the RF antennas each being configured to communicate in a same frequency band. The wireless charging device is configured to: communicate with the battery aligned with a first of the wireless charging bays using the RF antenna associated with the first wireless charging bay during a first period while preventing the RF antenna associated with a second of the wireless charging bays from communicating with the battery aligned with the second wireless charging bay; and responsive to the first period elapsing, communicate with the battery aligned with the second wireless charging bay using the RF antenna associated with the second wireless charging bay during a second period while preventing the RF antenna associated with the first wireless charging bay from communicating with the battery aligned with the first wireless charging bay.

In a further aspect, a method for managing communication with and charging of a plurality of wirelessly chargeable batteries for powering surgical instruments using a wireless charging device is provided, where the wireless charging device includes at least three wireless charging bays each for receiving different one of the batteries, a plurality of power transfer coils with each of the wireless charging bays being associated with a different one of the power transfer coils for charging the battery received by the wireless charging bay, and a plurality of RF antennas with each of the wireless charging bays being associated with a different one of the RF antennas for communicating with the battery received by the wireless charging bay. The method comprises: initiating a plurality of permission tokens corresponding to available RF communication slots for the wireless charging bays, the number of permission tokens being less than the number of wireless charging bays; and determining that communication permission is requested for the RF antenna associated with a first of the wireless charging bays. The method further includes, responsive to determining that communication permission is requested for the RF antenna associated with the first wireless charging bay, assigning a first of the permission tokens to the first wireless charging bay for a first period for granting permission for the RF antenna associated with the first wireless charging bay to communicate with a battery received by the first wireless charging bay; responsive to assigning the first permission token to the first wireless charging bay, determining that a second of the permission tokens is unassigned; and responsive to determining that the second permission token is unassigned, determining that communication permission is requested for the RF antenna associated with a second of the wireless charging bays. The method also includes, responsive to determining that communication permission is requested for the RF antenna associated with the second wireless charging bay, assigning the second permission token to the second wireless charging bay for a second period for granting permission for the RF antenna associated with the second wireless charging bay to communicate with a battery received by the second wireless charging bay; after assigning the second permission token to the second wireless charging bay, determining that the first period has elapsed; and responsive to determining that the first period has elapsed, revoking the first permission token from the first wireless charging bay. The method further includes, responsive to revoking the first permission token: charging the battery received by the first wireless charging bay; and assigning the first permission token to a third of the wireless charging bays for granting permission for a third period for the RF antenna associated with the third wireless charging bay to communicate with a battery received by the third wireless charging bay.

In another aspect, a wireless charging device for communicating with and charging a plurality of wirelessly chargeable batteries for powering surgical instruments is provided. The wireless charging device includes a housing defining a plurality of wireless charging bays each for receiving and charging one of the batteries; a plurality of power transfer coils disposed in the housing, each of the wireless charging bays being associated with a different one of the wireless power transfer coils for wirelessly charging the battery received by the wireless charging bay; a plurality of RF antennas disposed in the housing, each of the wireless charging bays being associated with a different one of the RF antennas for wirelessly communicating with the battery received by the wireless charging bay according to a proximity-based wireless communications protocol, the RF antennas each being configured to communicate in a same frequency band; and a main controller disposed in the housing. The main controller is configured to: grant permission for the RF antenna associated with a first of the wireless charging bays to communicate with a battery for powering a surgical instrument received by the first wireless charging bay for a first period while preventing the RF antenna associated with a second of the wireless charging bays from communicating with a battery for powering a surgical instrument received by the second wireless charging bay; and responsive to the first period elapsing, grant permission for the RF antenna associated with the second wireless charging bay to communicate with the battery for powering a surgical instrument received by the second wireless charging bay for a second period while preventing the RF antenna associated with the first wireless charging bay from communicating with the battery received by the first wireless charging bay.

DETAILED DESCRIPTION

Figure 1:
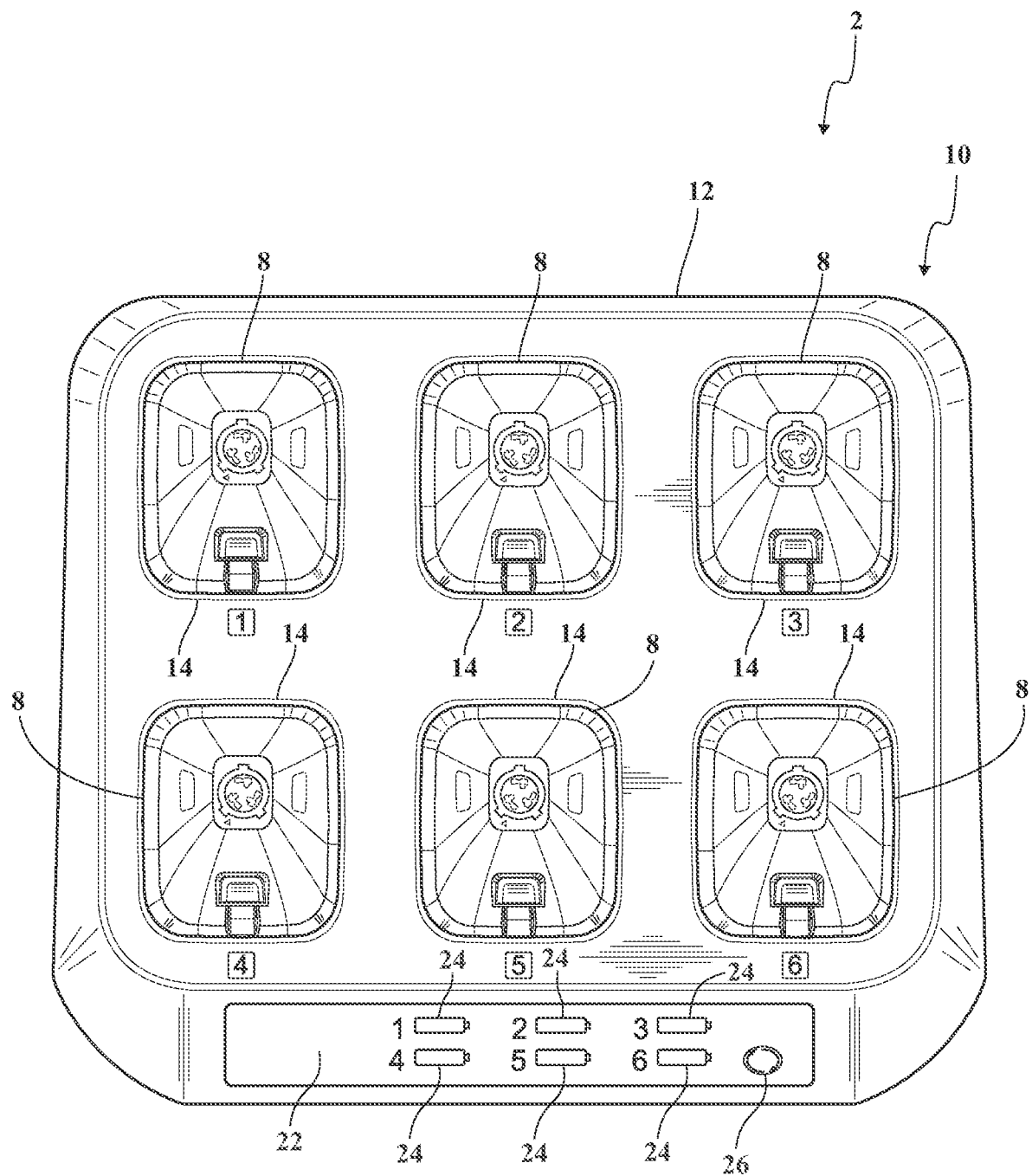
FIG. 1 illustrates an exemplary wireless charging system including a plurality of batteries for powering surgical instruments and a wireless charging device for receiving and charging the surgical batteries.
Figure 2:
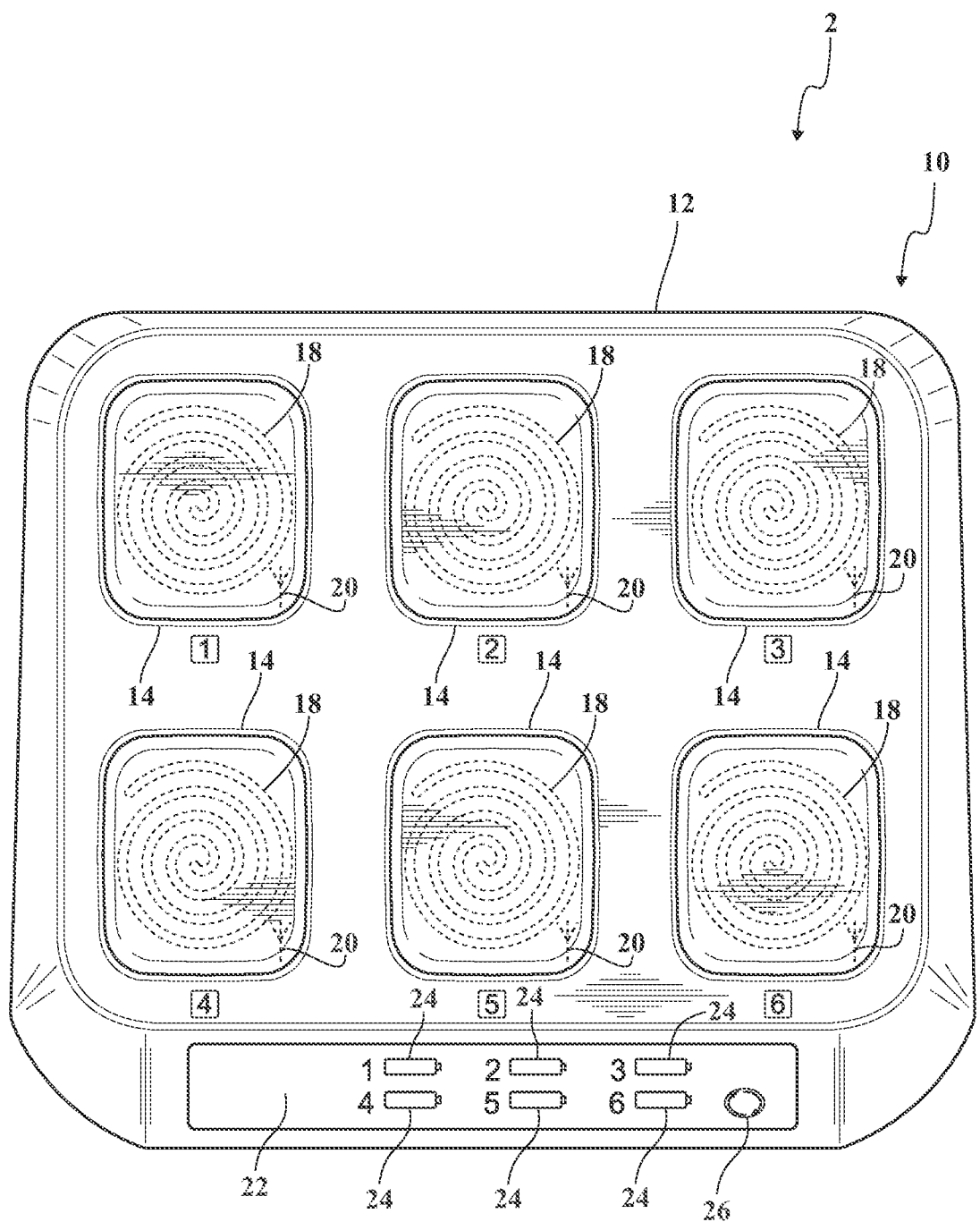
FIG. 2 illustrates the wireless charging device of FIG. 1 without having received the surgical batteries.

Referring to FIGS. 1 and 2, a wireless charging system 2 may include a plurality of wirelessly chargeable batteries 8 for powering surgical instruments, and a wireless charging device 10 for receiving and charging the batteries 8. In connection with charging the batteries 8, the wireless charging device 10 may also be configured wirelessly communicate with the received batteries 8, such as according to an RF communications protocol. For example and without limitation, the wireless charging device 10 may be configured to read data from a given battery 8 that includes, without limitation, an identity and/or signature of the battery 8, such as for authentication, and a state of the battery 8, such as a charge state. Based on such data, the wireless charging device 10 may verify that the received battery 8 is specifically designed for the surgical instruments it is intended to power, and may regulate its charging so as to prolong the life and capacity of the battery 8, which in turn reduces the number of battery swaps that may need to be performed during a surgical procedure.

The wireless charging device 10 may include a housing 12 defining a plurality of wireless charging bays 14, each being configured to receive a battery 8 for charging. The wireless charging device 10 may also include a plurality of wireless power transfer coils 18 disposed in the housing 12, and may include a plurality of RF antennas 20 disposed in the housing 12. Each of the wireless charging bays 14 may be associated with a different one of the wireless power transfer coils 18 for charging a battery 8 received in the wireless charging bay 14, and may be associated with a different one of the RF antennas 20 for wirelessly communicating with a battery 8 received in the wireless charging bay 14. The wireless transfer coils 18 may each be configured to charge a received battery 8 through an inductive coupling with the battery 8. The RF antennas 20 may each be configured to communicate with a received battery 8 using an RF communications protocol, or more particularly an RF proximity-based communications protocol, such as RFID or NFC. In this way, each RF antenna 20 may be configured to provide data communication between the medical wireless charging device 10 and a given battery 8 upon the battery 8 being received in the wireless charging bay 14 associated with the RF antenna 20. Each RF antenna 20 may be configured to communicate in a same frequency band, and/or at a substantially same frequency, such as about 13.56 MHz.

In some implementations, the plurality of wireless charging bays 14 may include at least three or at least four wireless charging bays 14 for receiving and charging at least three or at least four batteries 8 respectively. For instance, as shown in the illustrated example, the plurality of wireless charging bays 14 may consist of six wireless charging bays 14 for receiving and charging six batteries 8 at substantially the same time. Each of the plurality of wireless charging bays 14 may be within about 10 cm or less of one or more of the other wireless charging bays 14. For instance, as shown in the illustrated example, each of the plurality of wireless charging bays 14 may be within about 10 cm or less of each of three of the other wireless charging bays 14.

One concern with using RF communication between multiple transmitters and receivers operating within proximity of each other and at a similar frequency is co-channel interference (CCI). CCI can cause a disruption to the RF communication state machine, and therefore cause problems in communication between each transmission and reception of all hosts and endpoints. There is also an additive effect with the co-existing electromagnetic waves that causes an unfavorable amount of electromagnetic interference, which can result in poor operation or malfunction of the wireless charging device 10 when charging or communicating with a received battery 8. As a result, the battery 8 may fail to fully charge, have a reduced lifespan, or develop a reduced charge capacity, each of which may affect the ability of the battery 8 to effectively power a surgical instrument. The wireless charging device 10 may be configured to reduce or prevent these issues by dynamically and intelligently scheduling its wireless charging and data communication functions for each received battery 8, and thereby limit the number of RF antennas 20 that may be active at the same time.

The wireless charging device 10 may also include a user interface (UI) 22 for displaying information relating to operation of the wireless charging device 10. For instance, the UI 22 may include an indicator 24 for each of the wireless charging bays 14 that is configured to provide information relating to the wireless charging bay 14, such as a status of a battery 8 received in the wireless charging bay 14. For example and without limitation, the indicator 24 for each wireless charging bay 14 may be configured to indicate one or more of whether a battery 8 is received in the wireless charging bay 14, a state of the charge of the battery 8 received in the wireless charging bay 14, or a state of the health of the battery 8 received in the wireless charging bay 14, such as by illuminating the indicator 24 in accordance with the different states. To this end, the wireless charging device 10 may include one or more LEDs or other light source for each indicator 24 that illuminates all or a portion of the indicator 24 in accordance with the above states. In other examples, the indicators 24 may be implemented as part of a graphical user interface (GUI) implemented on a display of the UI 22.

Additionally or alternatively, the UI 22 may be configured for receiving user input for controlling operation of the wireless charging device 10. For instance, as shown in the illustrated example, the UI 22 may include a refresh button 26 that a user may select or press to initiate a refresh of a display area of the UI 22, responsive to which the wireless charging device 10 may be configured to re-determine and re-display the state(s) of each wireless charging bay 14 discussed above. In some instances, the UI 22 may include mechanical input elements, such as the refresh button 26 realized as a physical button, for receiving user input. Additionally or alternatively, the UI 22 may include a display with a touch screen interface that presents virtual input elements, such as the refresh button 26 realized as a virtual button, for receiving user input.

In addition to being configured to receive and charge batteries 8 directly, the wireless charging device 10, or more particularly the wireless charging bays 14, may be configured to receive and charge batteries 8 contained in a medical package configured to hold the batteries 8 in a sterilized state. More specifically, the wireless charging device 10 may be configured to receive a medical package holding one or more batteries 8 in a sterilized state, such that the one or more batteries 8 are aligned with and in close enough proximity of one or more of the wireless charging bays 14 to enable wireless communication with and charging of the batteries 8 via the one or more wireless charging bays 14. The wireless charging device 10 may thus be configured charge the one or more batteries 8 without the one or more batteries 8 exiting the sterilized state. In other words, the wireless charging device 10 may charge the one or more batteries 8 through the medical package, such as via an inductive coupling between each battery 8 and the power transfer coil 18 associated with the wireless charging bay 14 aligned with the battery 8.

Figure 3:
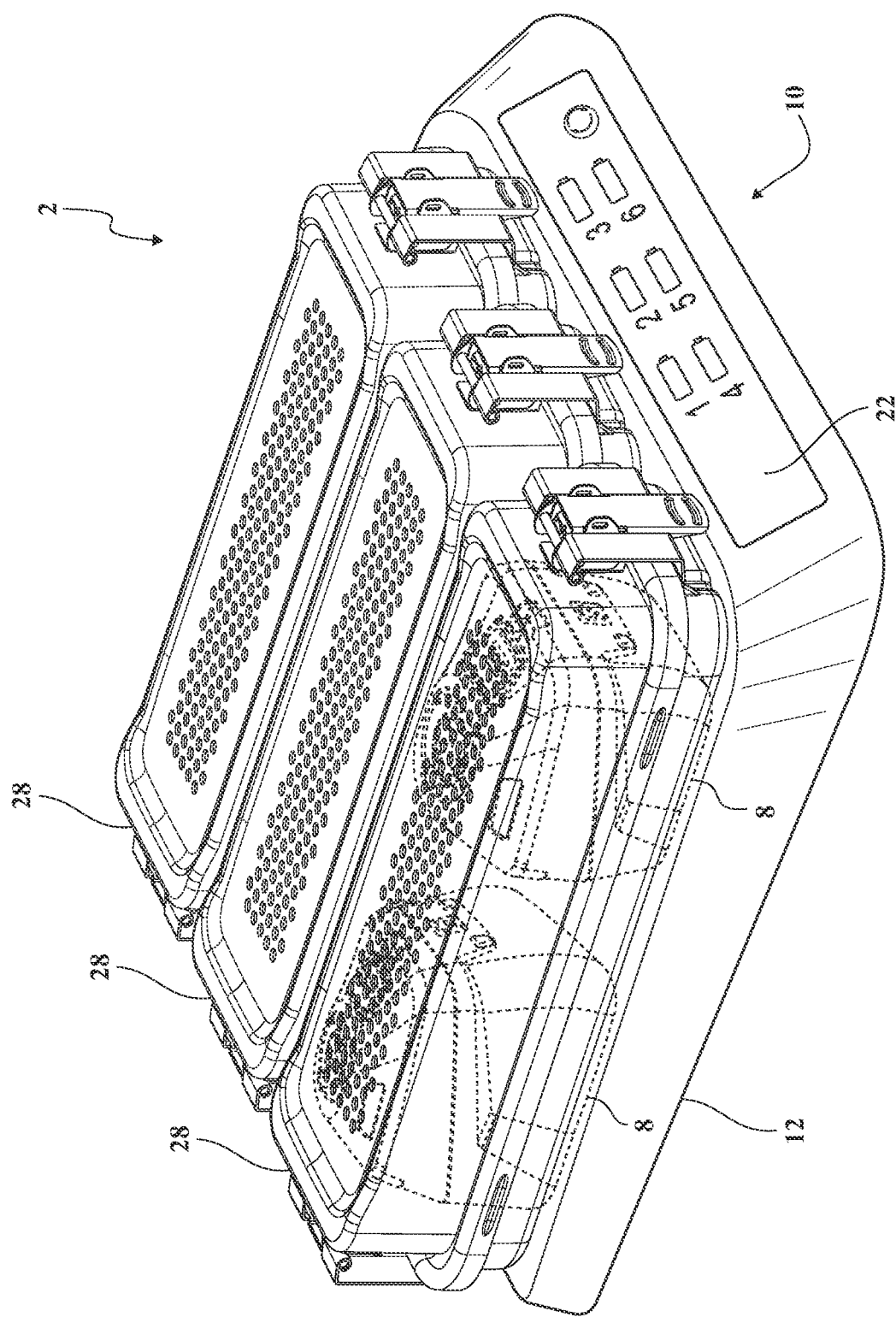
FIG. 3 illustrates the wireless charging system of FIG. 1 with the surgical batteries being received by the wireless charging device in a medical package for holding the batteries in a sterilized state.

Referring to FIG. 3, in some examples, the medical package may be realized as a sterilizable container 28 configured to receive one or more (e.g., two) batteries 8 for powering surgical instruments. The sterilizable container 28 holding the one or more batteries 8 may be placed in a sterilization process (e.g., autoclave process) in which the one or more batteries 8 and sterilizable container 28 are sterilized together. To this end, the sterilizable container 28 may be realized as an autoclavable container, such as that described in Applicant's PCT Publication No. WO 2020/198666 A2, the contents of which are hereby incorporated herein by reference in their entirety. Following the sterilization process, the sterilizable container 28 may be configured to maintain the one or more batteries 8 in a sterilized state, such as so long as the sterilizable container 28 remains sealed. The sterilizable container 28 holding the sterilized one or more batteries 8 may then be received by the wireless charging device 10, which in turn may be configured to charge the one or more batteries 8 while the one or more batteries 8 remain microbially sealed within a sterile volume of the sterilizable container 28. The wireless charging device 10 may also be configured to communicate with the one or more batteries 8 housed in the sterilizable container 28 to obtain data as described above without breaking the sterile state of the one or more batteries 8.

In addition or alternatively to the sterilizable container 28 described above, a medical package holding the one or more batteries 8 and received by the wireless charging device 10 for charging and communicating with the same may be realized as other forms, such as blue-wrap applied to a battery 8 during a sterilization process.

Figure 4:
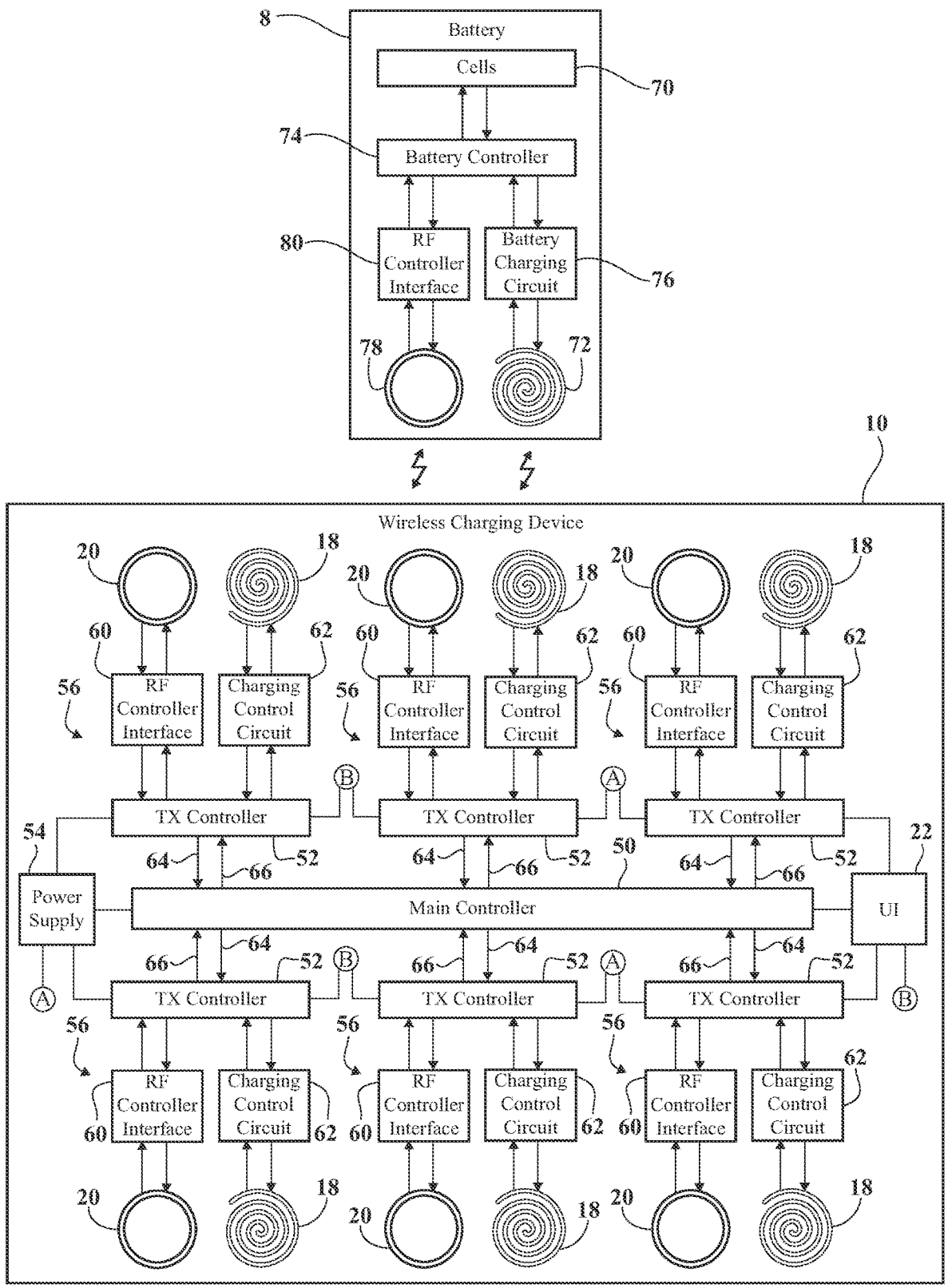
FIG. 4 illustrates exemplary components of the wireless charging system of FIG. 1.

FIG. 4 illustrates components that may be incorporated in the wireless charging device 10 and each of the batteries 8. As shown in the illustrated example, the wireless charging device 10 may include a main controller 50, a power supply 54, one or more control groups 56, and the UI 22. The main controller 50 may be electrically and/or communicatively coupled with each of the power supply 54, control group(s) 56, and power supply 54 to receive signals therefrom and/or control operation thereof. Each of the control group(s) 56 may likewise be electrically and/or communicatively coupled to the power supply 54 for receiving power therefrom and/or to the UI 22 for controlling operation thereof.

The power supply 54 may be configured to power each of the other components of the wireless charging device 10, including the power transfer coils 18 and RF antennas 20, so as to enable the same to operate. For instance, the power supply 54 may include an AC/DC converter configured to receive a mains AC power signal, such as from an outlet, and generate one or more DC power signals from the AC power signal. The DC power signals may then be supplied to various other components of the wireless charging device 10 to power the same, as described in more detail below.

The wireless charging device 10 may include a control group 56 for each wireless charging bay 14, with the control group 56 associated with a given wireless charging bay 14 being configured to regulate the charging and data communication functions of wireless charging bay 14 relative to a received battery 8. In some implementations, each wireless charging bay 14, and correspondingly the power transfer coil 18 and RF antenna 20 for the wireless charging bay 14, may be associated with a different control group 56.

Each control group 56 may include the power transfer coil 18 associated with a given wireless charging bay 14, the RF antenna 20 associated with the given wireless charging bay 14, and a transmitter (TX) controller 52 coupled and generally configured to manage operation of the power transfer coil 18 and RF antenna 20, such as to wirelessly charge and communicate with a battery 8 received by the given wireless charging bay 14. As the TX controller 52 may be configured to regulate the charging and communication functions of the given wireless charging bay 14 associated with the TX controller 52, the TX controller 52 may also be referred to as a "bay controller" herein.

Each control group 56 may also include an RF controller interface 60 coupled between the TX controller 52 and RF antenna 20. In some instances, the TX controller 52 and RF controller interface 60 may be configured to communicate via I2C. During operation of the wireless charging device 10, the TX controller 52 may be configured to enable and disable wireless communication via the RF antenna 20 by issuing various commands to the RF controller interface 60 that advance or retreat an RF state machine of the RF controller interface 60. One such command may be an RF enable command, which may cause the RF controller interface 60 to enable the RF antenna 20 coupled thereto to transmit and/or receive RF signals, such as to poll for and/or communicate with a battery 8 received in the associated wireless charging bay 14. Another command may be an RF disable command, which may cause the RF controller interface 60 to disable the RF antenna 20 so that no RF signals are transmitted and/or received via the RF antenna 20. The TX controller 52 of a given control group 56 may thus be configured to enable and disable the RF antenna 20 of the control group 56, such as by communicating corresponding commands to the RF controller interface 60 coupled to the RF antenna 20.

Similarly, each control group 56 may include a charging control circuit 62 coupled between the TX controller 52 and the power transfer coil 18 of the control group 56. Responsive to detecting that a battery 8 has been received in the wireless charging bay 14 associated with the charging control group 56, and to authenticating the battery 8, such as based on data received from the battery 8 via the RF antenna 20, the TX controller 52 may be configured to operate the charging control circuit 62 to develop an AC signal across the power transfer coil 18, which in turn may induce an electromagnetic field that charges the received battery 8. The TX controller 52 of a given control group 56 may thus be configured to enable and disable the power transfer coil 18 of the control group 56, such as by communicating corresponding commands to the charging control circuit 62 coupled to the power transfer coil 18.

For instance and without limitation, the charging control circuit 62 may include an DC/AC converter, a current sensor and/or a voltage sensor, and a charging controller coupled to the DC/AC converter and sensor(s). Responsive to receiving an enabling signal from the TX controller 52, the charging controller may be configured to provide a DC signal generated by the power supply 54 to the DC/AC converter, which in turn may generate an AC signal across the power transfer coil 18. The charging controller may then be configured to regulate the current through and/or power supplied by the power transfer coil 18 by regulating operation of the DC/AC converter based on data received form the current and/or voltage sensors. In some instances, the charging controller may also regulate the developed current and/or power based on data received from the battery 8 via the RF antenna 20 between charging cycles, such as data indicative of a current charge state of the battery 8.

Since multiple RF antennas 20 may need to communicate with received batteries 8 in real-time over the same frequency band, the main controller 50 may be configured to cooperate with the control groups 56 to implement a time sharing scheme for engaging in data communications. More particularly, each TX controller 52 may be coupled to the main controller 50, which may be configured to indicate to the TX controller 52 whether RF communication is permitted for the control group 56 of the TX controller 52. For instance, each TX controller 52 may be coupled to the main controller 50 via a harness with general purpose input/output (GPIO) pins, namely, a TX to Main pin and a Main to TX pin. Each TX controller 52 may be configured to assert a request signal 64 to the main controller 50 through the associated TX to Main Pin that is indicative of whether communication permission is requested for the RF antenna 20 of the control group 56 of the TX controller 52. Similarly, the main controller 50 may be configured to assert a permission signal 66 to each TX controller 52 through the associated Main to TX pin indicative of whether communication permission is granted for the RF antenna 20 of the control group 56 of the TX controller 52.

Thus, in tandem with the TX controllers 52 of the control groups 56 managing operation of the communication and charging functions of each wireless charging bay 14, the main controller 50 may function as a master for setting which RF antennas 20 may be active at a given time. More specifically, using a real-time operating system task, the main controller 50 may be configured to devise a time slicing schedule. For instance, the main controller 50 may be configured to permit the RF antenna 20 associated with one of the wireless charging bays 14 to communicate with a battery 8 received by and/or aligned with the wireless charging bay 14 for a limited period, which may be considered as a time slice assigned to the control group 56 of the RF antenna 20, while preventing the RF antenna 20 associated with another wireless charging bay 14 from communicating with a battery 8 received by and/or aligned with the another wireless charging bay 14, such as for the same period. Thereafter, responsive to the limited period elapsing, the main controller 50 may be configured to permit the RF antenna 20 associated with the another wireless charging bay 14 to communicate with the battery 8 received by and/or aligned with the another wireless charging bay 14 for a further period, which may be considered as a further time slice assigned to the control group 56 of the RF antenna 20 associated with the another wireless charging bay 14, while preventing the RF antenna 20 associated with the previous wireless charging bay 14 from communicating with the battery 8 received by and/or aligned with the previous wireless charging bay 14, such as for the further period.

Such functionality may be implemented through the request signals 64 and permission signals 66 described above. For instance, responsive to receiving a request for communication permission from the TX controller 52 of a given control group 56, such as via the TX controller 52 configuring the associated request signal 64 to high, the main controller 50 may be configured to determine whether an open time slice is available. If so, then the main controller 50 may be configured to grant permission for the TX controller 52 to initiate RF communication, such by setting the associated permission signal 66 to high. The TX controller 52 may then enable the RF antenna 20 coupled thereto by sending a corresponding signal to the RF controlled interface 60 operating the RF antenna 20 as described above.

Once a control group 56, or more particularly the RF antenna 20 of the control group 56, has completed its desired communication activities (e.g., the TX controller 52 has received desired data from a battery 8), the TX controller 52 may be configured to set the associated request signal 64 to low. In response, the main controller 50 may be configured to revoke the RF time slice form the control group 56, such as by setting the associated permission signal 66 to low. Alternatively, if the control group 56 violates its assigned time slice (e.g., reaches the time slice limit), then the main controller 50 may be configured to revoke the time slice from the control group 56, notwithstanding the status of the associated request signal 64, such as by setting the associated permission signal 66 to low. In either case, responsive to the time slice being revoked, the TX controller 52 may be configured to issue the RF disable command to the RF controller interface 60, which in turn may cease RF communications by the RF antenna 20.

To further reduce electromagnetic interface, when a given control group 56 is permitted to engage in RF communication with a received battery 8, the TX controller 52 of the given control group 56 may be configured to disable and prevent the power transfer coil 18 of the control group 56 from charging the battery 8. Similarly, when a given control group 56 is not permitted to engage in RF communications with a received battery 8, the TX controller 52 of the control group 56 may be configured to charge the battery 8 as described above. Thus, continuing with the example above in which the main controller 50 permits the RF antenna 20 associated with an initial wireless charging bay 14 to engage in wireless communication for an initial period and thereafter permits the RF antenna 20 associated with another wireless charging bay 14 to engage in wireless communication for another period, during the initial period, the TX controller 52 associated with the another wireless charging bay 14 may be configured to operate the power transfer coil 18 associated with the another wireless charging bay 14 to charge the battery 8 received by the another wireless charging bay 14, and the TX controller 52 associated with the initial wireless charging bay 14 may be configured to simultaneously prevent the wireless power transfer coil 18 associated with the initial wireless charging bay 14 from charging the battery 8 received by the initial wireless charging bay 14. Similarly, during the another period, the TX controller 52 associated with the initial wireless charging bay 14 may be configured to operate the power transfer coil 18 associated with the initial wireless charging bay 14 to charge the battery 8 received by the initial wireless charging bay 14, and the TX controller 52 associated with the another wireless charging bay 14 may be configured to simultaneously prevent the wireless power transfer coil 18 associated with the another wireless charging bay 14 from charging the battery 8 received by the another wireless charging bay 14.

In some instances, the main controller 50 may be configured to assign multiple communication time slices at a given time, thereby allowing multiple control groups 56 to engage in RF communication at the same time. In other words, the main controller 50 may be configured to permit a set number (e.g., three or less) of RF antennas 20 to communicate with received batteries 8 at the same time. In addition, although each control group 56 is described above as being associated with a single wireless charging bay 14, in other examples, a given control group 56 may be associated with a plurality of the wireless charging bays 14 for regulating the communication and charging functions of each. In this case, for each of the wireless charging bays 14 associated with a given control group 56, the control group 56 may include an RF controller interface 60, a charging control circuit 62, a power transfer coil 18, and an RF antenna 20 configured as described above, each of which may be coupled to a single TX controller 52 or distinct TX controllers 58 of the control group 56 for controlling and/or operating the same. Responsive to the main controller 50 assigning a time slice to such a control group 56, such as responsive to a TX controller 52 of the control group 56 asserting a request for communication permission, each of the wireless charging bays 14, or more particularly each of the RF antennas 20, of the control group 56 may be permitted to engage in RF communications with a received battery according to the assigned time slice, as described above.

Each battery 8 received by the wireless charging device 10 may include one or more power storage cells 70, a power receiving coil 72, and a battery controller 74 coupled to the power storage cells 70 and power receiving coil 72 to manage the same. The power receiving coil 72 may generally correspond to the power transfer coils 18 of the wireless charging device 10. As described above, during a charging cycle initiated by a TX controller 52 to charge a given battery 8, an AC signal may be generated across the power transfer coil 18 associated with the TX controller 52. This AC signal may induce a corresponding AC signal in the power receiving coil 72 of the battery 8, which in turn may be coupled to a battery charging circuit 76. The battery charging circuit 76 may be configured to rectify the received AC signal, which may then be applied, such as via the battery controller 74, to the power storage cells 70 to charge the same.

The battery 8 may also include an RF antenna 20 coupled to the battery controller 74, such as via an RF controller interface 80. Similar to the RF antennas 20 of the wireless charging device 10, the RF antenna 20 may be configured to implement a proximity-based wireless RF communications protocol, such as RFID or NFC. When the battery 8 is received in a wireless charging bay 14, the RF antenna 78 may come into communication range of the RF antenna 20. The battery controller 74 may then be configured to operate the RF antenna 78 via the RF controller interface 80, such as similar to the manner that the RF antenna 20 is operated above. As a result, wireless communication may be established between the battery controller 74 and the TX controller 52 via the RF antennas 20, 78.

Figure 5:
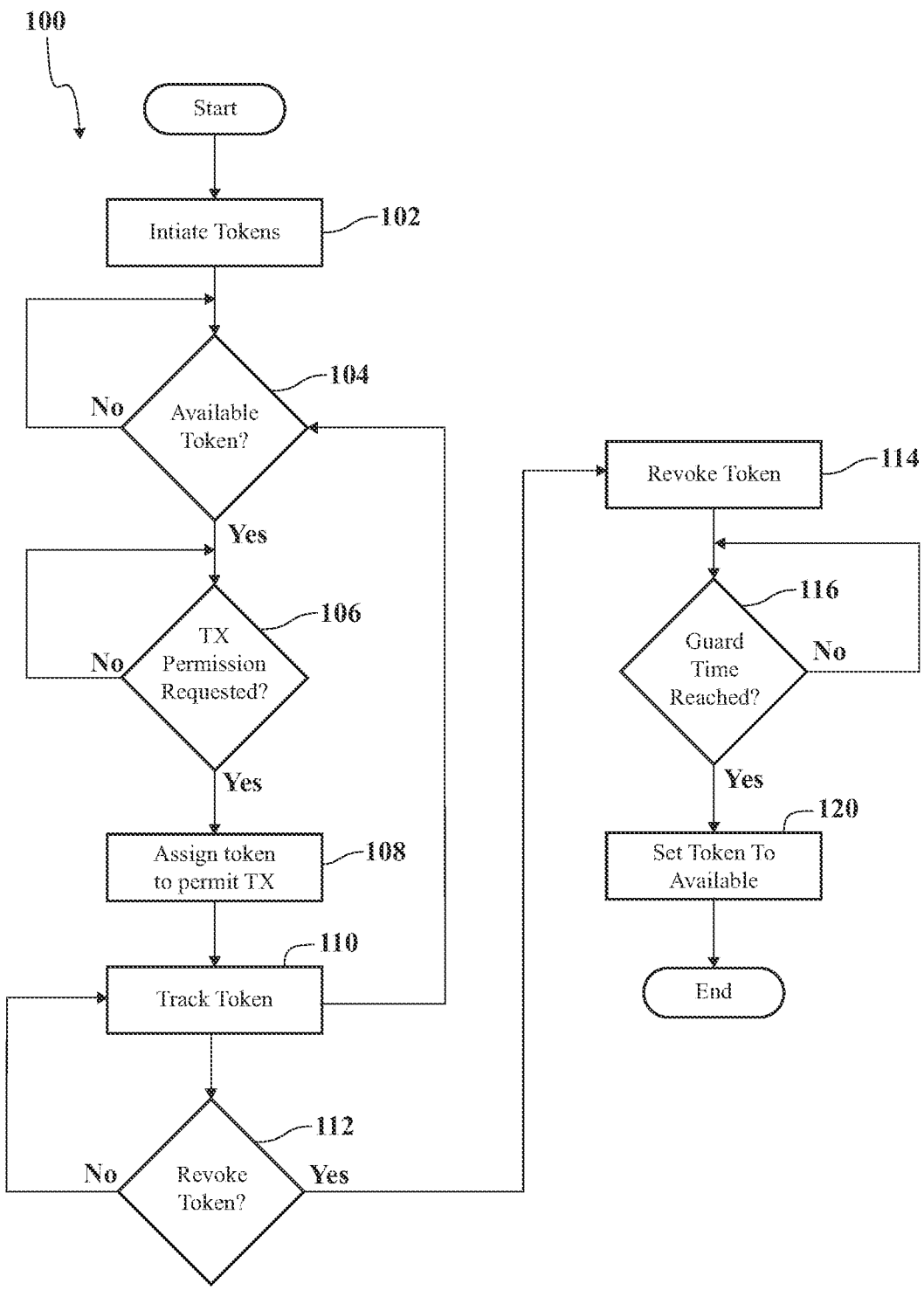
FIG. 5 illustrates an exemplary method 100 for allocating communication privileges between control groups of the wireless charging device of FIG. 1.

FIG. 5 illustrates a method 100 for allocating communication privileges between control groups 56, or more particularly wireless charging bays 14 of the control groups 56, of the wireless charging device 10. The method 100 may be implemented by the wireless charging device 10, or more particularly by the main controller 50.

In block 102, permission tokens may be initiated, such as by the main controller 50 upon startup of the wireless charging device 10. Each token may correspond to an available RF communication slot assignable by the main controller 50 to the control groups 56, or more particularly to the wireless charging bays 14 of the control groups 56, that grants permission for engaging in RF communication. The number of initiated tokens may correspond to the number of control groups 56 allowed to communicate with a battery 8 at a same time. For instance, initiation of three tokens upon startup may correspond to the main controller 50 being configured to permit the RF antennas 20 associated with three wireless charging bays 14 to communicate with batteries 8 received by the wireless charging bays 14 at the same time. In some examples, the main controller 50 may be configured to initiate the tokens by generating in memory an available token counter set equal to the number of available tokens.

In block 104, a determination may be made, such as by the main controller 50, of whether a token is currently available (i.e., unassigned to any control group 56). For instance, as each token is assigned to a control group 56, the token counter may be decremented to indicate that one less token is available. To determine whether a token is available for assignment, the main controller 50 may thus be configured to check whether the token counter is greater than zero, which may indicate that at least one token is available. During the first iteration through the method 100 after startup of the wireless charge device 10, a token will be determined available in block 104, as no tokens have yet been assigned. In later iterations, no token availability may be determined in block 104, such as if all tokens are currently assigned to control groups 56. Responsive to determining that no tokens are available ("No" branch of block 104), the method 100 may continue checking whether a token is available in block 104, until at least one token becomes available.

Responsive to determining that a token is available ("Yes" branch of block 104), in block 106, a determination may be made, such as by the main controller 50, of whether communication permission is being requested for a control group 56, or more particularly for the RF antenna 20 of a control group 56, such as to poll for and/or to retrieve data from a battery 8 received by the associated wireless charging bay 14. For instance, the main controller 50 may be configured to check the request signal 64 from each of the TX controllers 52 to determine whether the request signal 64 indicates the TX controller 52 is requesting communication permission. In some examples, the main controller 50 may be configured to traverse through the request signals 64 in a predetermined order. Thus, responsive to determining that communication permission is not being requested for an RF antenna 20 associated with a given wireless charging bay 14, the main controller 50 may be configured to determine whether communication permission is being requested for the RF antenna 20 associated with a next wireless charging bay 14 in the order, and so on until the main controller 50 reaches a request signal 64 indicating a request for communication permission or reaches the end of the order. In the latter case, the main controller 50 may be configured to start back at the beginning of the order.

Responsive to determining that communication permission is being requested for a given control group 56 ("Yes" branch of block 106), in block 108, the available token may be assigned, such as by the main controller 50, to the control group 56, so as to grant permission for the control group 56 to enable RF communication. In other words, the main controller 50 may be configured to grant communication permission for the RF antenna 20 associated with the wireless charging bay 14 for which permission was requested to communicate with or poll for a battery 8 received by the wireless charging bay 14. For instance, the main controller 50 may be configured to grant communication permission by configurating the permission signal 66 asserted by the main controller 50 to the corresponding TX controller 52 to indicate communication permission is granted (e.g. setting the permission signal 66 to high). Responsive to assigning an available token to a given control group 56, the main controller 50 may be configured to decrement the token counter by one, so as to facilitate the determination of available tokens in block 104 described above.

In block 110, the duration that the token is assigned to the given control group 56 may be tracked, such as by the main controller 50. More specifically, in order to fairly allocate communication permission between the different control groups 56, the main controller 50 may be configured to limit the duration in which a given control group 56 is granted communication permission. In other words, the main controller 50 may be configured to grant permission for a given RF antenna 20 to communicate for a limited period, also referred to herein as a "control group quantum." In some examples, the control group quantum for each assigned token may be greater than or equal to about 350 ms (e.g., between or equal to 350 ms±10 ms) and less than or equal to about 450 ms. (e.g., between or equal to 450 ms±10 ms). More specifically, the control group quantum for each assigned token may be about 400 ms (e.g., between or equal to 400 ms±10 ms).

As shown in the illustrated example, following block 110, the method 100 may return to block 104 to continue iterations of checking for and assigning available tokens, as described above. In other words, responsive to granting communication permission for the RF antenna 20 associated with a given wireless charging bay 14, assuming at least one token is determined available in block 104, the main controller 50 may be configured to determine whether communication permission is being requested for the RF antenna 20 associated with another wireless charging bay 14, as described above. To this end, the main controller 50 may again traverse through the control groups 56, such as according to the predefined order described above, to determine whether communication permission is being requested for an RF antenna 20 for which a token is not already assigned. If so, then the main controller 50 may be configured to assign the available token and grant communication permission for the control group 56 encompassing the RF antenna 20 for a limited period, such as by configuring the corresponding permission signal 66 to indicate such permission is granted. Assuming the main controller 50 is configured to assign multiple tokens at a same time, because the main controller 50 may assign given token before the control group quantum of a previously assigned token has elapsed, the periods in which the control groups 56 are granted permission to engage in RF communication may at least partially overlap.

In parallel with checking for further available tokens and assigning the same as described above, relative to each token assigned in block 108 and tracked in 110, in block 112, a determination may be made, such as by the main controller 50, of whether to revoke the token from the currently assigned control group 56. For instance, the main controller 50 may be configured to determine whether the control group quantum associated with the assigned token has elapsed, in which case the main controller 50 may be configured to withdraw permission for the RF antenna 20 of the control group 56 to engage in RF communication. Additionally or alternatively, the main controller 50 may be configured to monitor the request signal 64 from the TX controller 52 of the control group 56 to which the token is assigned to determine whether the TX controller 52 is no longer requesting RF communication permission. If so, then the main controller 50 may be configured to withdraw permission for the RF antenna 20 of the control group 56 to engage in RF communication by revoking the assigned token.

Responsive to determining not to revoke the token from the given control group 56 ("No" branch of block 112), the method 100 may continue tracking the token in block 110, as described above. Alternatively, responsive to determining to revoke the token from a given control group 56 ("Yes" branch of block 112), in block 114, the token may be withdrawn, such as by the main controller 50. For instance, the main controller 50 may be configured to configure the permission signal 66 asserted to the corresponding TX controller 52 to indicate that RF communication permission is not granted. In some instances, the main controller 50 may be configured to configure such permission signal 66 by setting the permission signal 66 to low (e.g. substantially zero volts).

In block 116, a determination may be made of whether a predefined guard time has been reached for the withdrawn token, such as by the main controller 50. The guard time may correspond to a period in which the withdrawn token is not assigned to any control group 56 following it being revoked. The guard time is intended to allow the control group 56, or more particularly the TX controller 52 of the control group 56, from which the token was revoked time to disable its RF antenna 20 from engaging in RF communications prior to initiating another RF antenna 20. In some examples, the guard time may be about 20 ms (e.g., between or equal to 20 ms±1 ms) or more. The main controller 50 may thus be configured to determine whether a duration from the revocation of the token in block 114 is greater than or equal to the guard time.

Responsive to determining that the guard time for the withdrawn token has been reached or exceed ("Yes" branch of block 116), in block 120, the withdrawn token may again be set, such as by the main controller 50, to available. For instance, the main controller 50 may be configured to increment the token counter to indicate that an additional token is now available.

Figure 6:
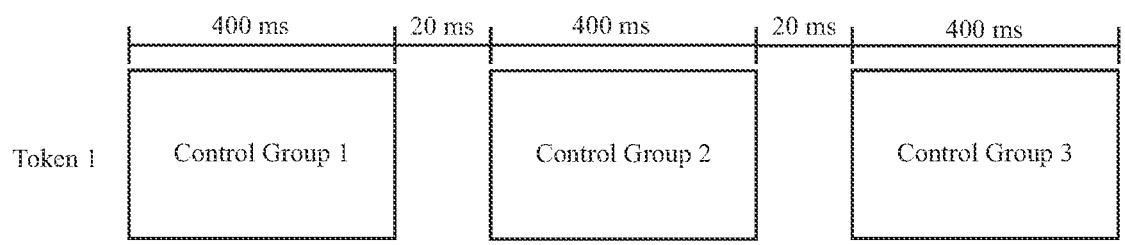
FIG. 6 illustrates a communication schedule that may be implemented by the method of FIG. 5.

FIG. 6 illustrates an exemplary RF communication allocation schedule 140 that may be implemented by the method 100, such as when the number of tokens initiated in block 102 is equal to one and the wireless charging device 10 includes at least three control groups 56. In other words, the RF communication allocation schedule 140 may correspond to the main controller 50 allowing only one control group 56, or more particularly the RF antenna 20 associated with only one wireless charging bay 14, to engage in RF communications at a given time.

According to the exemplary RF communication allocation schedule 140, the main controller 50 may assign the token to a first control group 56 requesting RF communication permission for a limited period of 400 ms. Responsive to the period elapsing, the main controller 50 may revoke the token from the first control group 56 and wait a guard time of 20 ms. Thereafter, the main controller 50 may determine that a second control group 56 is requesting RF communication permission, and assign the token to the second control group 56 for a further limited period of 400 ms. Responsive to the period elapsing, the main controller 50 may again revoke the token from the second control group 56 and wait a guard time of 20 ms. Thereafter, the main controller 50 may determine that a third control group 56 is requesting RF communication permission, and assign the token to the third control group 56 for a further limited period of 400 ms.

Figure 7:
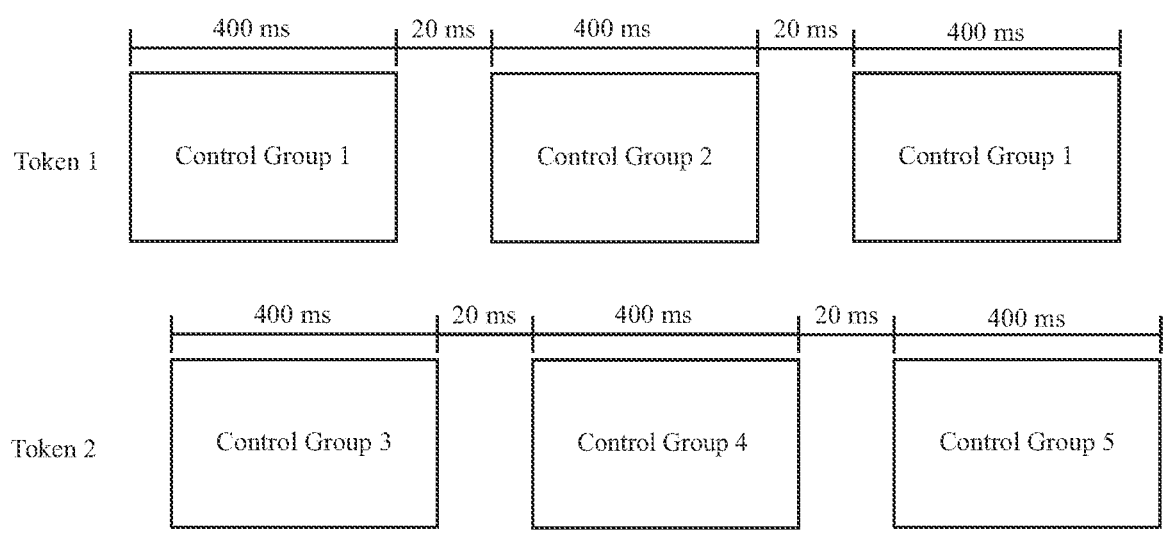
FIG. 7 illustrates a further communication schedule that may be implemented by the method of FIG. 5.

FIG. 7 illustrates another exemplary RF communication allocation schedule 160 that may be implemented by the method 100, such as when the number of tokens initiated in block 102 is equal to three and the wireless charging device 10 includes at least five control groups 56. In other words, the RF communication allocation schedule 160 may correspond to the main controller 50 allowing two control groups 56, or more particularly the RF communication antenna 20 associated with only two wireless charging bays 14, to engage in RF communications at a given time.

According to the exemplary RF communication allocation schedule 160, the main controller 50 may assign a first token to a first control group 56 requesting RF communication permission for a limited period of 400 ms. During the period in which the first token is allocated to the first control group 56, the main controller 50 may determine that a second control group 56 is not requesting RF communication permission, and thereafter determine that a third control group 56 is requesting RF communication permission. Accordingly, the main controller 50 may assign a second token to the third control group 56.

Following the initial 400 ms period associated with the first token elapsing, the main controller 50 may revoke the first token from the first control group 56 and wait a guard time of 20 ms. Thereafter, the main controller 50 may determine that the second control group 56 is now requesting RF communication permission, and assign the token to the second control group 56 for a further limited period of 400 ms. During the guard time for the first token, the initial 400 ms period associated with the second token may elapse. The main controller 50 may responsively revoke the second token from the third control group 56 and wait a guard time of 20 ms. Thereafter, the main controller 50 may determine that the fourth control group 56 is requesting RF communication permission, and assign the token to the fourth control group 56 for a further limited period of 400 ms.

Following the further 400 ms period associated with the first token elapsing, the main controller 50 may revoke the first token from the second control group 56 and wait another guard time of 20 ms. Thereafter, the main controller 50 may determine that the first control group 56 is again requesting RF communication permission (such as due to the battery 8 received in the associated wireless charging bay 14 being swapped out), and again assign the first token to the first control group 56 for another 400 ms period. During the guard time for the first token, the further 400 ms period associated with the second token may elapse. The main controller 50 may responsively revoke the second token from the fourth control group 56 and wait a guard time of 20 ms. Thereafter, the main controller 50 may determine that the fifth control group 56 is requesting RF communication permission, and assign the token to the fifth control group 56 for a further limited period of 400 ms.

Figure 8:
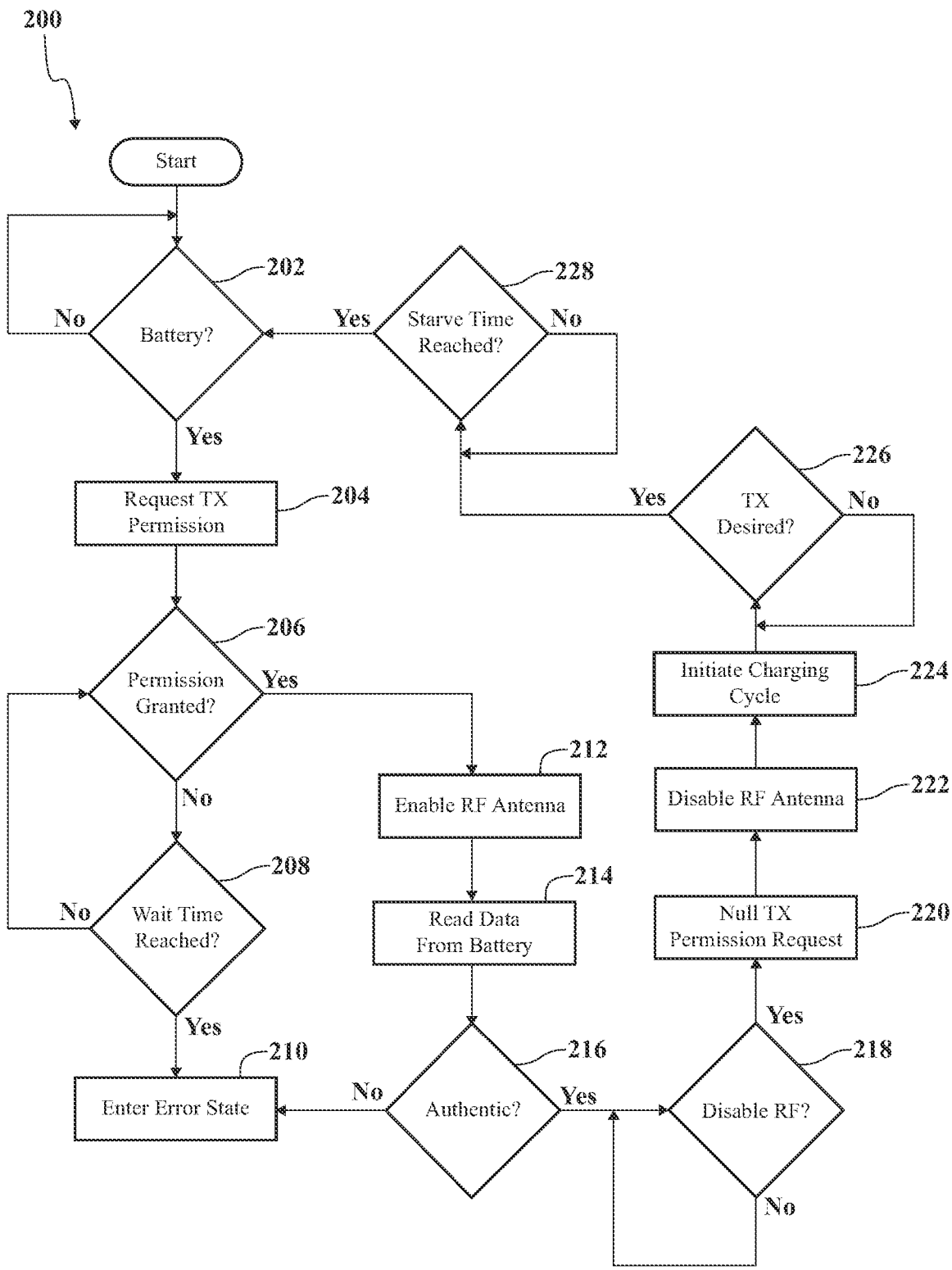
FIG. 8 illustrates an exemplary method for operating an RF antenna of the wireless charging device of FIG. 1 for communicating with a surgical battery received by the wireless charging device.

FIG. 8 illustrates a method 200 for managing RF communication with and charging of a battery 8 received by the wireless charging device 10. The method 200 may be performed by each control group 56, or more particularly by each TX controller 52 of the wireless charging device 10. It will thus be appreciated that the method 200 may be considered in reference to operation of one of the TX controllers 52 of the wireless charging device 10; however, each of the TX controllers 52 may be configured to perform the method 200 as described below.

In block 202, a determination may be made, such as by the TX controller 52, of whether a battery 8 has been received by the wireless charging bay 14 associated with the TX controller 52. For instance, the TX controller 52 may be configured to periodically scan for presence of a battery 8 by causing the charging control circuit 62 associated with the TX controller 52 to periodically output an AC signal across the associated power transfer coil 18, and then measuring the current being drawn through the power transfer coil 18. When a battery 8 is positioned in the wireless charging bay 14, the AC signal generated across the power transfer coil 18 may induce a corresponding AC signal across the power receiving coil 72 of the battery 8. Correspondingly, the current drawn through the power transfer coil 18 may increase. The TX controller 52 may thus be configured to determine whether a battery 8 has been received by a wireless charging bay 14 by determining whether the measured current drawn through the power transfer coil 18 increases to a value greater than a predefined threshold value corresponding to the presence of a battery 8. If so, then the TX controller 52 may be configured to determine that a battery 8 has been received in the associated wireless charging bay 14. Alternatively, the TX controller 52 may be configured to determine the presence of a battery 8 using the RF antenna 20, described in more detail below.

Responsive to determining that a battery 8 is received in the wireless charging bay 14 ("Yes" branch of block 202), in block 204, permission to engage in RF communication for the RF antenna 20 associated with the wireless charging bay 14 may be requested, such as by the TX controller 52. For instance, the TX controller 52 may be configured to request such permission from the main controller 50, such as by configuring the request signal 64 to the main controller 50 to indicates such request.

In block 206, a determination may be made, such as by the TX controller 52, of whether permission for engaging in RF communication has been granted. For instance, the TX controller 52 may be configured to check whether the permission signal 66 from the main controller 50 indicates that permission has been granted.

Responsive to determining that permission has not been granted ("No" branch of block 206), in block 208, a determination may be made, such as by the TX controller 52, of whether a predefined wait time has been reached since the time in which permission was requested in block 204. The predefined wait time may function to implement a guard dog protocol that determines an error if permission is not received by the TX controller 52 within a certain period of requesting permission. Such an event may indicate the existence of an issue relating to the TX controller 52, such as an open circuit between the main controller 50 and the TX controller 52. The wait time may be defined based on the duration of the control group quantum for each token, the number of available tokens, and the number of wireless charging bays 14 of the wireless charging device 10. As an example, the wait time may be equal to the control group quantum multiplied by double the number of wireless charging bays 14 divided by the number of tokens.

Thus, responsive to requesting RF communication permission in block 204, the TX controller 52 may be configured to track a duration from the request and compare the duration to the predefined wait time. Responsive to the comparison indicating that the duration is greater than or equal to the predefined wait time, the TX controller 52 may be configured to determine that the wait time has been reached in block 208.

Responsive to determining that the wait time has not been reached ("No" branch of block 208), the method 200 may return to block 206 to again determine whether RF communication permission has been granted, as described above. Conversely, responsive to determining that the wait time has been reached ("Yes" branch of block 208), in block 210, an error state may be entered into, such as by the TX controller 52. For instance, the TX controller 52 may be configured to disable the RF communication and charging functions for the wireless charging bay 14. The TX controller 52 may further be configured to provide an indication of the error on the UI 22, such as by communicating a signal thereto that causes the UI 22 to illuminate the indicator 24 corresponding to the wireless charging bay 14 in a color corresponding to the error.

Referring again to block 206, responsive to determining that permission has been granted ("Yes" branch of block 206), in block 212, the RF antenna 20 associated with the wireless charging bay 14 may be enabled, such as by the TX controller 52. For instance, the TX controller 52 may be configured signal the RF control interface 60 coupled to the RF antenna 20 to initiate RF communication with the battery 8.

As mentioned above, the determination of whether a battery 8 has been received in the wireless charging bay 14 in block 102 may be made by monitoring the current through the power transfer coil 18. In an alternative example, the TX controller 52 may be configured to determine whether a battery 8 has been received in the associated wireless charging bay 14 by being configured to periodically poll for a battery 8 using the RF antenna 20. More specifically, the TX controller 52 may be configured to periodically request permission to engage in RF communication using its associate RF antenna 20 as described above. Responsive to receiving such permission from the main controller 50, the TX controller 52 may be configured to signal the RF controller interface 60 to enable the RF antenna 20 and poll for a battery 8, such as by transmitting an interrogation signal. Responsive to receiving a response to the interrogation signal via the RF antenna 20 from a battery 8, the TX controller 52 may be configured to determine that a battery 8 is present in the wireless charging bay 14.

Continuing with the method 200, in block 214, data may be read, such as by the TX controller 52, from the battery 8 over the RF antenna 20. As non-limiting examples, the read data may include authentication data and/or status data of the battery 8 described above. In block 216, a determination may be made, such as by the TX controller 52, of whether the battery 8 is authentic based on read data. For instance, the TX controller 52 may be configured to apply a verification algorithm to the authentication data, which may indicate whether the battery 8 is authentic. Responsive to determining that the battery 8 is not authentic ("No" branch of block 216), in block 210, an error state may be entered into, such as by the TX controller 52. For instance, the TX controller 52 may be configured to disable the RF communication and charging functions of the associated wireless charging bay 14. The TX controller 52 may also be configured to provide an indication of the error on the UI 22, such as by communicating a signal to the UI 22 that cause the UI 22 to illuminate the indicator 24 corresponding to the wireless charging bay 14 in a color corresponding to the authentication error.

Conversely, responsive to determining that the battery 8 is authentic ("Yes" branch of block 216), in block 218, a determination may be made, such as by the TX controller 52, of whether to disable the RF antenna 20. For instance, the TX controller 52 may be configured to determine to disable the RF antenna 20 responsive to completion of its RF communication activities (e.g., reading and verifying of data from the battery 8). Additionally or alternatively, the TX controller 52 may be configured to determine to disable the RF antenna 20 responsive to receiving a permission signal 66 form the main controller 50 indicative that RF communication permission is no longer granted.

Responsive to determining to disable the RF antenna 20 ("Yes" branch of block 218), in block 220, the RF transmission request may be nulled, as by the TX controller 52. For instance, the TX controller 52 may be configured to set the request signal 64 between the TX controller 52 and the main controller 50 to indicate that RF communication permission is no longer being requested. In block 222, the RF antenna 20 may be disabled, such as by the TX controller 52. For instance, the TX controller 52 may be configured to assert a command to the RF controller interface 60 coupled to the RF antenna 20 that advances the state machine for the RF antenna 20 to a disabled state. Correspondingly, no transmissions may be sent from or received by the RF antenna 20. In block 224, a charging cycle may be initiated, such as by the TX controller 52. For instance, the TX controller 52 may activate the charging control circuit 62, which may then function to charge the power storage cells 70 of the battery 8 as described above. In some examples, the charging control circuit 62 may consider the latest status data read from the battery 8 to determine how to regulate the current through and/or power supplied by the power transfer coil 18.

In block 226, following initiation of a charging cycle, a determination may be made, such as by the TX controller 52, of whether RF communication permission is again desired for the control group 56. For instance, the TX controller 52 may be configured to periodically request RF communication permission at regular time intervals, such as to read updated status data from the battery 8 and/or the authentication data to further verity that the battery 8 is authentic. Additionally or alternatively, the TX controller 52 may be configured to request RF communication permission responsive to the power signal supplied by the power transfer coil 18 satisfying certain characteristic(s), such as a predefined amount of power or current being supplied through the power transfer coil 18 since the beginning of the charging cycle. Responsive to any one or more of these events, the TX controller 52 may be configured to determine that RF communication permission is desired.

Responsive to determining that RF communication permission is desired ("Yes" branch of block 226), in block 228, as determination may be made, such as by the TX controller 52, of whether a starve time has been reached. The starve time may correspond to a period in which the TX controller 52 is not allowed to request RF communication permission following the RF antenna 20 being disabled, such as to enable other control groups 56, or more particularly wireless charging bays 14, to have a chance to obtain RF communication permission. In some examples, the starve time may be about 10 ms (e.g., between or equal to 10 ms±1 ms). The TX controller 52 may thus be configured to track a duration since the RF antenna 20 was disabled, and compare the duration to the starve time to determine whether the tracked duration is greater than or equal to the starve time. If so, then the TX controller 52 may be configured to determine that the starve time has been reached.

In some instances, block 228 may also consider the guard time described above. The guard time may represent a period in which the main controller 50 prevents a withdrawn token from being marked available and reassigned. The TX controller 52 may thus be configured to track a duration from which a token is revoked from the TX controller 52, and in block 228, compare the duration to a period of time equal to the sum of the guard and starve times to determine whether the duration is greater than or equal to the sum. If so, then the TX controller 52 may be configured to determine that the starve time has been reached.

Responsive to determining that the starve time has been reached ("yes" branch of block 228), the method may return to block 202 to determine whether a battery 8 continues to be received in the associated wireless charging bay 14; if so, request RF communication permission in block 204, and so on.

Aspects of the present disclosure describe unique and specific protocols for managing RF communication between multiple wireless charging bays of a wireless charging device and multiple surgical instrument batteries so as to mitigate co-channel and electromagnetic interference. Such RF communication is more reliable as a result, and lends to the improved charging, use, and lifespan of the surgical instrument batteries.

As one non-limiting example, each controller 50, 52, 74 may include a processor, memory, and non-volatile storage. The processor may include one or more devices selected from microprocessors, micro-controllers, digital signal processors, microcomputers, central processing units, field programmable gate arrays, programmable logic devices, state machines, logic circuits, analog circuits, digital circuits, and/or any other devices that manipulate signals (analog or digital) based on operational instructions read into the memory, such as from the non-volatile storage. The memory may include a single memory device or a plurality of memory devices including, but not limited to, read-only memory (ROM), random access memory (RAM), volatile memory, non-volatile memory, static random access memory (SRAM), dynamic random access memory (DRAM), flash memory, cache memory, and/or any other device capable of storing information. The non-volatile storage may include one or more persistent data storage devices such as a hard drive, optical drive, tape drive, non-volatile solid state device, and/or any other device capable of persistently storing information.

The processor may be configured to read into memory, such as from the storage, and operate under control of software embodied by computer-executable instructions. The computer-executable instructions may be compiled or interpreted from a variety of programming languages and/or technologies, including, without limitation, and either alone or in combination, Java, C, C++, C #, Objective C, Fortran, Pascal, Java Script, Python, Perl, and PL/SQL. The computer-executable instructions may be configured, upon execution by the processor, to cause the processor to implement the functions, features, processes, and methods of the respective controller 50, 52, 74 described herein. In this way, the respective controller 50, 52, 74, or more particularly the processor of the respective controller 50, 52, 74, may be considered as being configured or programmed to implement the functions, features, processes, and methods of the components of the wireless charging system 2 described herein.

In various configurations, the functionality of each controller 50, 52, 74 may be distributed among multiple controllers that are connected together. For example, multiple controllers 50, 52, 74 may implement the same functionality distributed by a load balancing system. Additionally or alternatively, the functionality of two or more of the controllers 50, 52, 74 may be combined and implemented by a single controller.

In general, the routines executed to implement aspects of foregoing description, whether implemented as part of an operating system or a specific application, component, program, object, module or sequence of instructions, or even a subset thereof, may be referred to herein as "computer program code," or simply "program code." Program code may comprise computer readable instructions that are resident at various times in various memory and storage devices in a computer or controller and that, when read and executed by one or more processors in a computer or controller, cause that computer or controller to perform the operations necessary to execute operations and/or elements embodying the various aspects of the description. Computer readable program instructions for carrying out operations of the various aspects of the description may be, for example, assembly language or either source code or object code written in any combination of one or more programming languages.

The program code embodied in any of the applications/modules described herein may be capable of being individually or collectively distributed as a program product in a variety of different forms. In particular, the program code may be distributed using a computer readable storage medium having computer readable program instructions thereon for causing a processor to carry out aspects of the description.

Computer readable storage media, which is inherently non-transitory, may include volatile and non-volatile, and removable and non-removable tangible media implemented in any method or technology for storage of information, such as computer-readable instructions, data structures, program modules, or other data. Computer readable storage media may further include random access memory (RAM), read-only memory (ROM), erasable programmable read-only memory (EPROM), electrically erasable programmable read-only memory (EEPROM), flash memory or other solid state memory technology, portable compact disc read-only memory (CD-ROM), or other optical storage, magnetic cassettes, magnetic tape, magnetic disk storage or other magnetic storage devices, or any other medium that can be used to store the desired information and which can be read by a computer or controller. A computer readable storage medium should not be construed as transitory signals per se (e.g., radio waves or other propagating electromagnetic waves, electromagnetic waves propagating through a transmission media such as a waveguide, or electrical signals transmitted through a wire). Computer readable program instructions may be downloaded to a computer or controller, another type of programmable data processing apparatus, or another device from a computer readable storage medium or to an external computer or controller or external storage device via a network.

Computer readable program instructions stored in a computer readable medium may be used to direct a computer or controller, other types of programmable data processing apparatus, or other devices to function in a particular manner, such that the instructions stored in the computer readable medium produce an article of manufacture including instructions that implement the functions/acts specified in the flowcharts, sequence diagrams, and/or block diagrams. The computer program instructions may be provided to one or more processors such that the instructions, which execute via the one or more processors, cause a series of computations to be performed to implement the functions and/or acts specified in the flowcharts, sequence diagrams, and/or block diagrams described herein.

In certain alternatives, the functions and/or acts described herein, such as in connection with a process or method, and/or specified in the flowcharts, sequence diagrams, and/or block diagrams may be re-ordered, processed serially, and/or processed concurrently without departing from the scope of the present disclosure. Moreover, any of the processes, methods, flowcharts, sequence diagrams, and/or block diagrams may include more or fewer blocks pr steps than those illustrated herein.

The terminology used herein is for the purpose of describing particular examples only and is not intended to be limiting. As used herein, the singular forms "a," "an," and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. Furthermore, to the extent that the terms "includes," "having," "has," "with," "comprised of," or variants thereof are used in either the detailed description or the claims, such terms are intended to be inclusive in a manner similar to the term "comprising."

While a description of various examples has been provided and while these examples have been described in considerable detail, it is not the intention of the Applicant to restrict or in any way limit the scope of the appended claims to such detail. Additional advantages and modifications will readily appear to those skilled in the art. The present disclosure in its broader aspects is therefore not limited to the specific details, representative apparatus and method, and illustrative examples shown and described. Accordingly, departures may be made from such details without departing from the spirit or scope of the Applicant's general inventive concept.

Certain aspects of the present disclosure can be described with reference to the following clause:

Clause 1. A wireless charging system comprising a plurality of wirelessly chargeable batteries for powering surgical instruments, a medical package holding the batteries in a sterilized state, and a wireless charging device configured to receive the medical package holding the batteries in the sterilized state for charging the batteries without the batteries exiting the sterilized state. The wireless charging device comprises: a housing defining a plurality of wireless charging bays for charging the batteries, the wireless charging bays arranged so that each of the batteries aligns with a different one of the wireless charging bays when the medical package holding the batteries in the sterilized state is received by the wireless charging device; a plurality of power transfer coils disposed in the housing, each of the wireless charging bays being associated with a different one of the power transfer coils for wirelessly charging the battery aligned with the wireless charging bay; and a plurality of RF antennas disposed in the housing, each of the wireless charging bays being associated with a different one of the RF antennas for wirelessly communicating with the battery aligned with the wireless charging bay according to a proximity-based wireless communications protocol, the RF antennas each being configured to communicate in a same frequency band. The wireless charging device is configured to: communicate with the battery aligned with a first of the wireless charging bays using the RF antenna associated with the first wireless charging bay during a first period; and communicate with the battery aligned with the second wireless charging bay using the RF antenna associated with the second wireless charging bay during a second period, wherein the first and second time periods are different and do not overlap, and wherein only one of the RF antenna associated with the first wireless charging bay and the RF antenna associated with the second wireless charging bay is active during the first time period and the second time period.

What is claimed is:

1. A wireless charging system comprising:
   a plurality of wirelessly chargeable batteries for powering surgical instruments;
   a medical package holding the batteries in a sterilized state; and
   a wireless charging device configured to receive the medical package holding the batteries in the sterilized state for charging the batteries without the batteries exiting the sterilized state, the wireless charging device comprising:
      a housing defining a plurality of wireless charging bays for charging the batteries, the wireless charging bays arranged so that each of the batteries aligns with a different one of the wireless charging bays when the medical package holding the batteries in the sterilized state is received by the wireless charging device;
      a plurality of power transfer coils disposed in the housing, each of the wireless charging bays being associated with a different one of the power transfer coils for wirelessly charging the battery aligned with the wireless charging bay; and
      a plurality of RF antennas disposed in the housing, each of the wireless charging bays being associated with a different one of the RF antennas for wirelessly communicating with the battery aligned with the wireless charging bay according to a proximity-based wireless communications protocol, the RF antennas each being configured to communicate in a same frequency band,
   wherein the wireless charging device is configured to:
      communicate with the battery aligned with a first of the wireless charging bays using the RF antenna associated with the first wireless charging bay during a first period while preventing the RF antenna associated with a second of the wireless charging bays from communicating with the battery aligned with the second wireless charging bay; and
      responsive to the first period elapsing, communicate with the battery aligned with the second wireless charging bay using the RF antenna associated with the second wireless charging bay during a second period while preventing the RF antenna associated with the first wireless charging bay from communicating with the battery aligned with the first wireless charging bay.

2. The wireless charging system of claim 1, wherein the wireless charging device is configured to:
- charge the battery aligned with the second wireless charging bay using the power transfer coil associated with the second wireless charging bay during the first period while preventing with the power transfer coil associated with the first wireless charging bay from charging the battery aligned with the first wireless charging bay; and
- charge the battery aligned with the first wireless charging bay using the power transfer coil associated with the first wireless charging bay during the second period while preventing with the power transfer coil associated with the second wireless charging bay from charging the battery aligned with the second wireless charging bay.

3. The wireless charging system of claim 1, wherein the wireless charging device comprises a main controller configured to:
- determine whether communication permission is requested for the RF antenna associated with the first wireless charging bay;
- responsive to determining that communication permission is requested for the RF antenna associated with the first wireless charging bay, grant permission for the the RF antenna associated with the first wireless charging bay to communicate with the battery aligned with the first wireless charging bay for the first period;
- responsive to determining that communication permission is not requested for the RF antenna associated with the first wireless charging bay, determine whether communication permission is requested for the RF antenna associated with the second wireless charging bay; and
- responsive to determining that communication permission is requested for the RF antenna associated with the second wireless charging bay, grant permission for the RF antenna associated with the second wireless charging bay to communicate with the battery aligned with the second wireless charging bay for the second period.

4. The wireless charging system of claim 3, wherein the main controller is configured to:
- responsive to granting permission for the RF antenna associated with the first wireless charging bay to communicate with the battery aligned with the first wireless charging bay for the first period, determine whether communication permission is requested for the RF antenna associated with a third of the wireless charging bays; and
- responsive to determining that communication permission is requested for the RF antenna associated with the third wireless charging bay, grant permission for the RF antenna associated with the third wireless charging bay to communicate with the battery aligned with the third wireless charging bay for a third period that at least partially overlaps the first period.

5. The wireless charging system of claim 4, wherein the first period elapses after permission is granted for the RF antenna associated with the third wireless charging bay to communicate with the battery aligned with the third wireless charging bay for the third period, and the main controller is configured to, responsive to the first period elapsing:
- revoke permission for the RF antenna associated with the first wireless charging bay to communicate with the battery aligned with the first wireless charging bay; and
- responsive to revoking permission:
  - determine whether communication permission is requested for the RF antenna associated with the second wireless charging bay; and
  - responsive to determining that communication permission is requested for the RF antenna associated with the second wireless charging bay, grant permission for the RF antenna associated with the second wireless charging bay to communicate with the battery aligned with the second wireless charging bay for the second period.

6. The wireless charging system of claim 1, wherein the wireless charging device comprises a main controller configured to:
- initiate a plurality of permission tokens corresponding to available RF communication slots for the wireless charging bays, the number of permission tokens being less than the number of wireless charging bays;
- responsive to determining that communication permission is requested for the RF antenna associated with the first wireless charging bay, assign a first of the permission tokens to the first wireless charging bay for the first period;
- responsive to assigning the first permission token to the first wireless charging bay, determine whether a second of the permission tokens is unassigned;
- responsive to determining that the second permission token is unassigned, determine whether communication permission is requested for the RF antenna associated with a third of the wireless charging bays; and
- responsive to determining that communication permission is requested for the RF antenna associated with the third wireless charging bay, assign the second permission token to the third wireless charging bay.

7. The wireless charging system of claim 5, wherein the main controller is configured to:
- responsive to the first period elapsing, revoke the first permission token from the first wireless charging bay;
- responsive to revoking the first permission token from the first wireless charging bay, determine whether communication permission is requested for the RF antenna associated with the second wireless charging bay; and
- responsive to determining that communication permission is requested for the RF antenna associated with the second wireless charging bay, assign the first permission token to the second wireless charging bay.

8. The wireless charging system of claim 7, wherein the main controller is configured to, responsive to revoking the first permission token, prohibit reassignment of the first permission token for a third period from the revocation.

9. The wireless charging system of claim 8, wherein the third period is at least about 20 milliseconds.

10. The wireless charging system of claim 1, wherein the wireless charging device comprises a main controller and a plurality of bay controllers coupled to the main controller, each of the RF antennas being coupled to a different one of the bay controllers for enabling and disabling the RF antenna coupled to the bay controller,
- wherein each of the bay controllers is configured to assert a first signal to the main controller indicative of whether communication permission is requested for the RF antenna coupled to the bay controller, and
- wherein the main controller is configured, for each of the bay controllers, to assert a second signal to the bay controller indicative of whether communication permission is granted for the RF antenna coupled to the bay controller based on the first signal asserted by each of the bay controllers.

11. The wireless charging system of claim 10, wherein each of the bay controllers is configured to:
responsive to a battery being aligned with the wireless charging bay associated with the RF antenna coupled to the bay controller, detect the battery; and
responsive to detecting the battery, configure the first signal asserted by the bay controller to indicate that communication permission is requested for the RF antenna coupled to the bay controller.

12. The wireless charging system of claim 10, wherein each of the bay controllers is configured to:
responsive to the second signal asserted to the bay controller indicating that communication permission is granted, initiate wireless communication between the RF antenna coupled to the bay controller and the battery aligned with the wireless charging bay associated with the RF antenna; and
responsive to the second signal asserted to the bay controller subsequently indicating that communication permission is not granted:
disable the RF antenna coupled to the bay controller; and
configure the first signal asserted by the bay controller to indicate that communication permission is not requested for a least a third period.

13. The wireless charging system of claim 12, wherein third period is about 30 ms.

14. The wireless charging system of claim 10, wherein each of the bay controllers is configured to:
configure the first signal asserted by the bay controller to indicate that communication permission is requested for the RF antenna coupled to the bay controller;
responsive to the first signal asserted by the bay controller being configured to indicate that communication permission is requested for the RF antenna coupled to the bay controller, determine whether a third period has elapsed from when the first signal is configured to indicate that communication permission is requested; and
responsive to determining that the third period has elapsed, disable the wireless charging bay associated with the RF antenna coupled to the bay controller.

15. The wireless charging system claim 1, wherein the wireless charging bays comprise four wireless charging bays.

16. The wireless charging system of claim 15, wherein the wireless charging device is configured to enable no more than three of the RF antennas associated with the wireless charging bays at the same time.

17. The wireless charging system of claim 16, wherein each of the wireless charging bays is within about 10 cm of each of at least three of the other wireless charging bays.

18. The wireless charging system of claim 1, wherein each of the first period and the second period is greater than or equal to about 350 ms and less than or equal to about 450 ms.

19. A method for managing communication with and charging of a plurality of wirelessly chargeable batteries for powering surgical instruments using a wireless charging device, the wireless charging device including at least three wireless charging bays each for receiving different one of the batteries, a plurality of power transfer coils with each of the wireless charging bays being associated with a different one of the power transfer coils for charging the battery received by the wireless charging bay, and a plurality of RF antennas with each of the wireless charging bays being associated with a different one of the RF antennas for communicating with the battery received by the wireless charging bay, the method comprising:
initiating a plurality of permission tokens corresponding to available RF communication slots for the wireless charging bays, the number of permission tokens being less than the number of wireless charging bays;
determining that communication permission is requested for the RF antenna associated with a first of the wireless charging bays;
responsive to determining that communication permission is requested for the RF antenna associated with the first wireless charging bay, assigning a first of the permission tokens to the first wireless charging bay for a first period for granting permission for the RF antenna associated with the first wireless charging bay to communicate with a battery received by the first wireless charging bay;
responsive to assigning the first permission token to the first wireless charging bay, determining that a second of the permission tokens is unassigned;
responsive to determining that the second permission token is unassigned, determining that communication permission is requested for the RF antenna associated with a second of the wireless charging bays;
responsive to determining that communication permission is requested for the RF antenna associated with the second wireless charging bay, assigning the second permission token to the second wireless charging bay for a second period for granting permission for the RF antenna associated with the second wireless charging bay to communicate with a battery received by the second wireless charging bay;
after assigning the second permission token to the second wireless charging bay, determining that the first period has elapsed;
responsive to determining that the first period has elapsed, revoking the first permission token from the first wireless charging bay; and
responsive to revoking the first permission token:
charging the battery received by the first wireless charging bay; and
assigning the first permission token to a third of the wireless charging bays for granting permission for a third period for the RF antenna associated with the third wireless charging bay to communicate with a battery received by the third wireless charging bay.

20. A wireless charging device for communicating with and charging a plurality of wirelessly chargeable batteries for powering surgical instruments, the wireless charging device comprising:
a housing defining a plurality of wireless charging bays each for receiving and charging one of the batteries;
a plurality of power transfer coils disposed in the housing, each of the wireless charging bays being associated with a different one of the power transfer coils for wirelessly charging the battery received by the wireless charging bay;
a plurality of RF antennas disposed in the housing, each of the wireless charging bays being associated with a different one of the RF antennas for wirelessly communicating with the battery received by the wireless charging bay according to a proximity-based wireless communications protocol, the RF antennas each being configured to communicate in a same frequency band; and a main controller disposed in the housing and configured to:
  grant permission for the RF antenna associated with a first of the wireless charging bays to communicate with a battery for powering a surgical instrument received by the first wireless charging bay for a first period while preventing the RF antenna associated with a second of the wireless charging bays from communicating with a battery for powering a surgical instrument received by the second wireless charging bay; and
  responsive to the first period elapsing, grant permission for the RF antenna associated with the second wireless charging bay to communicate with the battery for powering a surgical instrument received by the second wireless charging bay for a second period while preventing the RF antenna associated with the first wireless charging bay from communicating with the battery received by the first wireless charging bay.

* * * * *